United States Patent
Jenkins

(10) Patent No.: US 7,156,099 B1
(45) Date of Patent: Jan. 2, 2007

(54) NOSTRIL FILTERING SYSTEM

(76) Inventor: Cloytillia M. Jenkins, 1104 Gittings Ave., Baltimore, MD (US) 21239

( * ) Notice: Subject to any disclaimer, the term of this patent is extended or adjusted under 35 U.S.C. 154(b) by 0 days.

(21) Appl. No.: 10/975,270

(22) Filed: Oct. 28, 2004

Related U.S. Application Data

(60) Provisional application No. 60/598,484, filed on Aug. 3, 2004.

(51) Int. Cl.
*A61G 10/00* (2006.01)
*A61M 16/00* (2006.01)
*A62B 7/10* (2006.01)
*A62B 23/02* (2006.01)

(52) U.S. Cl. .............. 128/206.11; 128/207.18; 128/205.29; 128/205.11; 128/205.25; 128/205.27; 128/206.12; 128/206.18; 128/206.21; 128/207.13; 128/204.12; 128/200.24; 128/201.25

(58) Field of Classification Search .......... 128/206.11, 128/205.29, 205.11, 205.25, 205.27, 206.12, 128/206.18, 206.21, 207.13, 207.18, 204.12, 128/200.24, 201.25

See application file for complete search history.

(56) References Cited

U.S. PATENT DOCUMENTS

| | | | | |
|---|---|---|---|---|
| 480,505 A * | 8/1892 | Midgley et al. | ....... | 128/204.13 |
| 513,458 A * | 1/1894 | Culhane | .............. | 606/199 |
| 810,617 A * | 1/1906 | Carence | ........... | 128/206.11 |
| 878,223 A * | 2/1908 | Meisselbach | ......... | 128/203.22 |
| 1,160,797 A * | 11/1915 | Wallin | ............... | 128/203.22 |
| 1,256,188 A * | 2/1918 | Wilson | ................ | 606/199 |
| 1,311,461 A * | 7/1919 | Reynard | ........... | 128/203.22 |
| 1,709,740 A * | 4/1929 | Rogers | ................ | 606/199 |
| 2,426,161 A * | 8/1947 | Biederman | ........ | 128/204.12 |
| 2,672,138 A * | 3/1954 | Pomeroy | ........... | 128/207.18 |
| 2,777,442 A * | 1/1957 | Zelano | ............ | 128/206.11 |
| 3,424,152 A * | 1/1969 | Kuhlman | ............. | 128/848 |
| 3,463,149 A * | 8/1969 | Theodor | ............ | 128/204.12 |
| 4,052,983 A * | 10/1977 | Bovender | .......... | 128/204.12 |
| 4,220,150 A * | 9/1980 | King | ................ | 128/206.11 |
| 4,221,217 A * | 9/1980 | Amezcua | ........... | 128/206.11 |
| 4,253,452 A * | 3/1981 | Powers et al. | ......... | 128/864 |
| 4,267,831 A * | 5/1981 | Aguilar | ............ | 128/203.14 |
| 4,327,719 A * | 5/1982 | Childers | ........... | 128/206.11 |
| 4,369,783 A * | 1/1983 | Hiller et al. | .......... | 604/11 |
| 4,887,597 A * | 12/1989 | Holland | ............ | 128/206.11 |
| D319,878 S * | 9/1991 | Holland | ............ | D24/106 |
| 5,775,335 A * | 7/1998 | Seal | ................ | 128/848 |
| 5,895,409 A * | 4/1999 | Mehdizadeh | ......... | 606/199 |
| 6,216,694 B1 | 4/2001 | Chen | | |
| 6,494,205 B1 * | 12/2002 | Brown | ............ | 128/206.11 |
| 6,561,188 B1 * | 5/2003 | Ellis | ............... | 128/206.11 |
| 6,562,057 B1 * | 5/2003 | Santin | ............. | 606/199 |
| 6,564,800 B1 * | 5/2003 | Olivares | ........... | 128/206.11 |
| 6,701,924 B1 * | 3/2004 | Land et al. | ......... | 128/206.11 |
| 6,971,388 B1 * | 12/2005 | Michaels | ........... | 128/206.11 |
| 6,978,781 B1 * | 12/2005 | Jordan | ............. | 128/206.11 |
| 2004/0089303 A1 * | 5/2004 | Chien | .............. | 128/206.11 |

* cited by examiner

*Primary Examiner*—Henry Bennett
*Assistant Examiner*—Nihir Patel
(74) *Attorney, Agent, or Firm*—Galbreath Law Offices, P.C; John A. Galbreath

(57) ABSTRACT

A nostril filtering system is described for providing clean, filtered air for breathing in through the nose. The filtering system includes a soft, pliable filter material held in a flexible frame that can be inserted into each nostril of a user. In the case of foul odors or noxious fumes, for example, the filter can include an activated charcoal filter portion. The device can be offered in several sizes to accommodate adults and children.

7 Claims, 2 Drawing Sheets

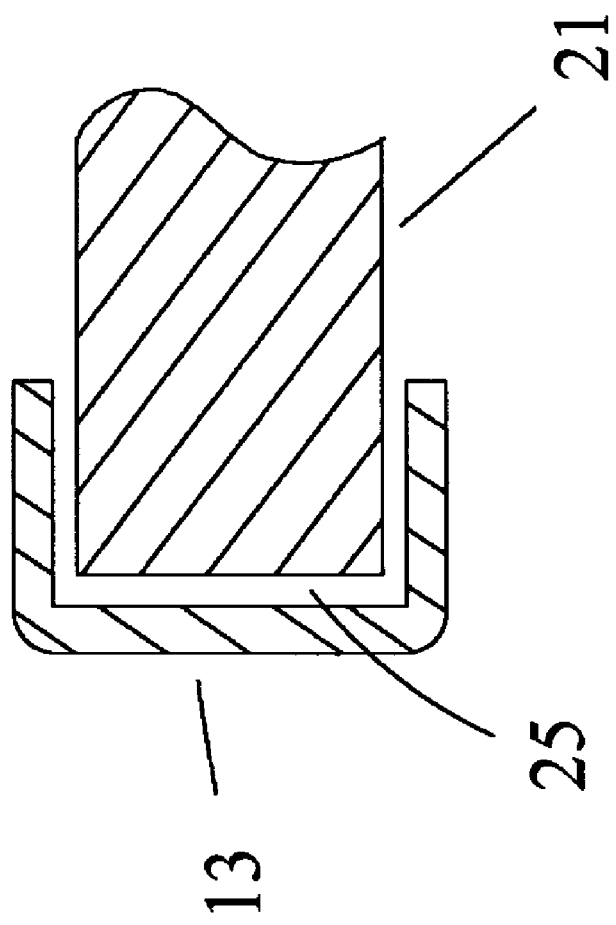

NOSTRIL FILTERING SYSTEM

CROSS REFERENCE TO RELATED APPLICATION

This application is based upon and claims benefit of co-pending U.S. Provisional Patent Application Ser. No. 60/598,484 entitled "Nostril Filtering System", filed with the U.S. Patent and Trademark Office on Aug. 3, 2004 by the inventor herein, the specification of which is incorporated herein by reference.

BACKGROUND OF THE INVENTION

1. Field of the Invention

The present invention relates to compact nasal inserts with incorporated filters, especially designed to provide consumers with a more user-friendly and cost effective means of blocking dust and pollen from entering the nasal cavities, as well as avoiding foul odors.

2. Background of the Prior Art

Allergies are among the most common of medical disorders. Abnormal reactions of the immune system which occur in response to otherwise harmless substances, it is estimated that 60 million Americans, or more than one in every five people, suffer from some form of allergy, with similar proportions throughout much of the rest of the world. In fact, allergy is the single largest reason for school absence and is a major source of lost productivity in the workplace. An allergy is a type of immune reaction. Normally, the immune system responds to foreign bodies, like pollen or bacteria, by producing specific proteins called antibodies that are capable of binding to identifying molecules (antigens) on the foreign body. This reaction between antibody and antigen sets off a series of reactions designed to protect the body from infection. Sometimes, this same series of reactions is triggered by harmless, everyday substances. This is the condition known as allergy, and the offending substance is called an allergen. Allergens enter the body through four main routes: the airways, the skin, the gastrointestinal tract, and the circulatory system.

The most common of allergens, airborne allergens cause the sneezing, runny nose, and itchy, bloodshot eyes of hay fever (allergic rhinitis). Whether dust, mold, pollen, or pet dander, airborne allergens can also affect the lining of the lungs, causing asthma, or the conjunctiva of the eyes, causing conjunctivitis (pink eye). To combat these nuisances in the home and avoid allergic reactions, many consumers employ equipment such as dehumidifiers to dry the air, thus extinguishing the environment for allergens to breed, as well as air purifiers that capture the airborne particles through a filtering system. While these devices are quite effective in reducing allergens in the home, they tend to be quite expensive, and are simply not practical for most allergy sufferers. In addition, dehumidifiers and air purifiers are not portable, so those who depend upon them find themselves at the mercy of allergens when going to work or attending to outside tasks and errands. Susceptible to reactions from airborne allergens swirling outside and in public buildings, allergy sufferers face daunting challenges whenever they leave the safety of home.

The use of nasal filters is known in the prior art. Generally, the devices heretofore devised and utilized for the purpose of filtering air breathed in through the nose are known to consist basically of familiar, expected, and obvious structural configurations. For example, there exist various nasal appliances for use in connection with filtering pollutants from the air.

U.S. Pat. No. 4,327,719, issued to Irene J. Childers, discloses a nose filter for filtering air breathed through the nostrils. The device includes a resilient nose fitted element with dual replaceable filter members and a central spring biasing connection member.

U.S. Pat. No. 6,216,694, issued to Jung-Fu Chen, discloses a stuff-in type nose plug with air filters that are integrally connected to each other at one end. The filter may have an active carbon portion fixed to the air inlet so that dirt and filthy air can be filtered before being inhaled by the user.

U.S. Pat. No. 6,701,924, issued to Richard D. Land, Jr. et al., discloses a nasal filter consisting of a spring clip having flanged ends with an oval shaped filter element on each end. The filter elements can be disposable separately from the spring clip.

While each of the above-mentioned devices may be effective to some degree in providing a nasal filter, none of the references, however, disclose a compact, inexpensive, and safe nostril filtering system that is worn essentially entirely within the nasal cavity such that it is virtually invisible.

SUMMARY OF THE INVENTION

The present invention provides a solution to the above and other problems by enabling a simply designed, easy to construct, and simple to wear nostril filtration device that can be quickly applied and removed and is effective to block out pollen, dust, mold, or pet dander in the home, office, outdoors, or in public places.

It is, therefore, an object of the present invention to enable a nostril filtering system that avoids the disadvantages of the prior art.

It is another object of the present invention to enable a nostril filtering system that is designed to provide a more pleasant intake of air. It is a related object of the present invention to enable a nostril filtering system that is designed to provide a healthier intake of air.

It is another object of the present invention to enable a nostril filtering system having a simple design. It is a related object of the present invention to enable a nostril filtering system having a simple filter material. It is a further related object of the present invention to enable a nostril filtering system using activated charcoal filtering material.

It is another object of the present invention to enable a nostril filtering system that may be easily and efficiently manufactured and marketed. A related object of the present invention is to enable a nostril filtering system that is susceptible of a low cost of manufacture with regard to both materials and labor, and which accordingly is then susceptible of low prices of sale to the consuming public, thereby making such a nostril filtering system economically available to the buying public.

In accordance with the above and other objects, a nostril filtering system is described for providing clean, filtered air for breathing in through the nose. With regard to a particularly preferred embodiment of the invention, the filtering system taught herein includes a soft, pliable filter material held in a flexible frame that can be inserted into each nostril of a user. In the case of foul odors or noxious fumes, for example, the filter can include an activated charcoal filter portion. The device can be offered in several sizes to accommodate adults and children.

The nostril filtering system would afford consumers a number of significant benefits and advantages. Foremost, the nostril filtering system would provide a simple, affordable means for allergy sufferers to combat airborne allergens at any time of day, wherever they may go. A compact filtering system that can be inserted directly into the nose, the nostril filtering system would offer a portable, low cost solution for blocking out pollen, dust, mold, or pet dander in the home, in the office, outdoors, or in other public buildings. In addition to fighting allergens, this versatile product's absorbency capabilities would also effectively resist foul odors. In this manner, non-allergic consumers could purchase the nostril filtering system to keep on hand whenever encountering a foul stench, such as driving through an area that reeks from pollution or odors emanating from crowds on public transportation. Extremely easy to use, a nostril filtering system insert can be applied and removed in just a matter of seconds. Safe for all users and offered in various sizes, this practical product would be ideal for children as well as adults. As an additional consideration, this product could be offered in several sizes to accommodate both child (under age twelve would require adult supervision) and adult users.

The nostril filtering system is an innovative appliance that offers allergy sufferers a more practical tool in the battle against airborne allergens. Lightweight and comfortable, this handy device would provide a portable filtering system whenever one is needed.

BRIEF DESCRIPTION OF THE DRAWINGS

The above and other features, aspects, and advantages of the present invention are considered in more detail, in relation to the following description of embodiments thereof shown in the accompanying drawings, in which:

FIG. 3 illustrates a cross-sectional view of the frame, showing the groove and the filter element insert that fits into the groove.

DETAILED DESCRIPTION OF THE INVENTION

The invention summarized above and defined by the enumerated claims may be better understood by referring to the following description, which should be read in conjunction with the accompanying drawings in which like reference numbers are used for like parts. This description of an embodiment, set out below to enable one to build and use an implementation of the invention, is not intended to limit the enumerated claims, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
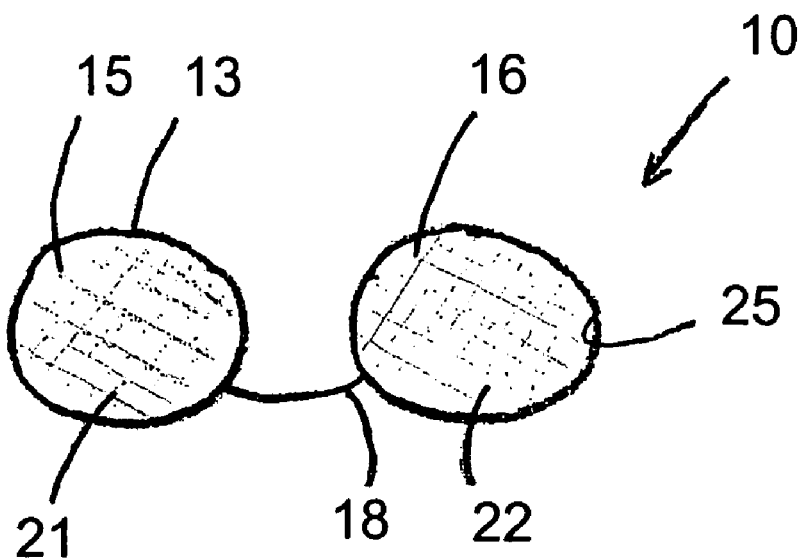
FIG. 1 illustrates an elevational view of a filter device according to one embodiment of the present invention.
Figure 2:
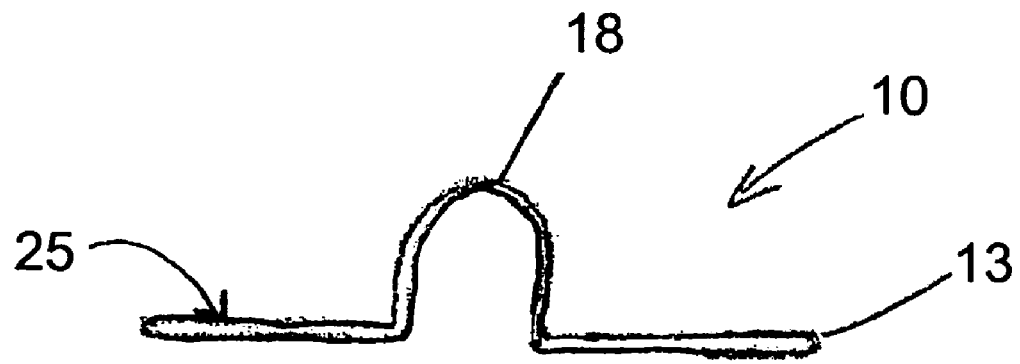
FIG. 2 illustrates a top plan view of a filter device according to one embodiment of the present invention.

Recognizing the need for an affordable and portable means of combating allergens, the present invention includes a line of compact nasal inserts with incorporated filters, specially designed to provide a more pleasant and healthy intake of air. Referring to FIGS. 1 and 2, a filtration device, indicated generally as 10, has a frame 13 comprising two substantially circular openings 15, 16 joined by a U-shaped connector 18. The frame 13 may be made of light plastic or wire and sized such that the openings 15, 16 are approximately ½-inch in diameter. Other appropriate sizes may be used to establish a range of sizes to fit the nostril opening of various users. Filter element inserts 21, 22 are largely fabricated of a soft, pliable filter material such as compressed cotton. The spacing of the passages through the filtering material is preselected such that the various types of particulate material can be filtered from the ambient atmosphere. For example, for small pollen matters the spacing should be very small to enhance the entrapping feature of the filter element inserts 21, 22. Additionally, the filtering material may include activated charcoal, long known by the medical industry to be a safe, effective filtering agent for extracting liquids and gases from their harmful elements. Each filter element insert 21, 22 would be comprised of two flat, round or oval-shaped filters. The inner portion of frame 13, on the side toward the openings 15, 16 there is a groove 25 around the inner circumference of the openings 15, 16. The filter element inserts 21, 22 defines a perimeter that rests in the groove 25. The filter element insets 21, 22 should be sufficiently rigid and thin to enable the perimeter of the filter element to fit and hold in the groove 25. The engagement between the filter element inserts 21, 22 and the groove 25 serves to prevent the passage of the filter element inserts 21, 22 through the frame 13, and positions the filter element inserts 21, 22 in the stream of air drawn into the user's nostril during inhalation. In a preferred embodiment, the filter element inserts can be removed from the openings and separately disposed while the frame portion can be re-used.

Use of the filtration device 10 would be very simple and straightforward. First, the user would select an appropriate filtration device 10 based on personal preference of size. By way of example, a mother may choose a small size package for her daughter who is allergic to dust. Similarly, a construction worker may need a larger unit for use when out on the job. Removing a filtration device 10 from its packaging, the user would simply insert the filtration device 10 into each nostril, pushing upward until the U-shaped connector 18 rests flushly against the septum of the nose, or the area between the nostrils. In a preferred embodiment, the filtration device 10 will be inserted approximately ¼ to ½-inch into the nostril. While inside the nose, the filter element inserts 21, 22 work to capture airborne allergens within its filters. When properly positioned, the filtration device 10 would provide protection for the user's respiratory system from potentially harmful debris and pollutants in the air. Because of the device's filtering capabilities, poor air would be filtered as it enters the user's nostrils, before it enters the user's airways. In addition, as the user inhales, the filter element inserts 21, 22 absorb pathogens and odors, attaching to them by chemical attraction. The surface area of activated charcoal gives it countless bonding sites, and when certain chemicals pass next to the carbon surface, they attach to the surface and are trapped. Thus, the filters cover up any external odors that may be circulating in the atmosphere and the user would be able to breathe clean air, which could improve overall health. After use, the filtration device can be easily removed, and simply discarded in a trash receptacle.

The filtration device 10 can also be used as a medicine delivery vehicle for medicine that is inhaled. For example, a user may apply a small amount of medicine, such as a few drops of a decongestant or antihistamine, to the filter element inserts 21, 22 before inserting the device into the nose. The medication would be breathed in normally over a longer period of time. A wide variety of medicinal applications may be used. Alternatively, a user may apply a small amount of perfume to the filter element inserts 21, 22 before inserting the device into the nose to provide a pleasant scent for the user while it is worn.

The invention has been described with references to a preferred embodiment. While specific values, relationships, materials and steps have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

What is claimed is:

1. The nostril filtering system for filtering air breathed through the nostrils, said system comprising:
    a frame, comprising:
    (1) a pair of substantially circular openings; and
    (2) a connector; and
    a filter element located in each of said pair of openings; said filter element having a diameter greater than its height wherein the connector is sized and configured to enable the frame to be inserted with one opening and filter element in each nostril of a user such that the connector rests against the septum of the nose of the user, and only said connector of said nostril filtering system is visible on the exterior surface of the nose; the sides of said frame being a solid band surrounding the filter elements;
    wherein said frame further comprising a groove on an inner portion of said opening and said filter element further defining a perimeter, wherein the perimeter portion of the filter element fits within said groove.

2. The nostril filtering system according to claim 1, the filter element further comprising an activated charcoal filter.

3. The nostril filtering system according to claim 1, wherein the filter element is made of absorptive material.

4. The nostril filtering system according to claim 1, wherein the frame is inserted approximately ¼ inch into the nose of the user.

5. The nostril filtering system according to claim 1, wherein said connector is substantially U-shaped.

6. The nostril filtering system according to claim 1, further comprising a medicinal application or said filter element located in each of said pair of openings.

7. The nostril filtering system according to claim 1, further comprising a perfume application on said filter element located in each of said pair of openings.

* * * * *